(12) United States Patent
Zhang et al.

(10) Patent No.: US 7,645,086 B2
(45) Date of Patent: Jan. 12, 2010

(54) DELIVERY TIP FOR FLOWABLE MATERIALS

(75) Inventors: Haiming Zhang, Hebei Province (CN); Steven D. Jensen, South Jordan, UT (US); Densen Cao, Sandy, UT (US)

(73) Assignee: CAO Group, Inc., West Jordan, UT (US)

( * ) Notice: Subject to any disclaimer, the term of this patent is extended or adjusted under 35 U.S.C. 154(b) by 248 days.

(21) Appl. No.: 11/743,115

(22) Filed: May 1, 2007

(65) Prior Publication Data

US 2008/0140030 A1 Jun. 12, 2008

Related U.S. Application Data

(63) Continuation-in-part of application No. 11/567,367, filed on Dec. 6, 2006, now Pat. No. 7,476,049.

(51) Int. Cl.
*A46B 11/00* (2006.01)
(52) U.S. Cl. ........................................ 401/290; 401/270
(58) Field of Classification Search ................. 401/268, 401/270, 290; 300/4, 5, 8; 15/205.2
See application file for complete search history.

(56) References Cited

U.S. PATENT DOCUMENTS

| | | | |
|---|---|---|---|
| 752,078 A * | 2/1904 | Burt et al. .................. 401/276 |
| 5,829,976 A | 11/1998 | Green | |
| 5,908,257 A | 6/1999 | Martin | |
| 6,049,934 A | 4/2000 | Discko | |
| 6,059,570 A | 5/2000 | Dragan et al. | |
| 6,315,483 B1 * | 11/2001 | Velliquette .................. 401/278 |
| 6,382,972 B1 | 5/2002 | Fischer et al. | |
| 6,390,817 B1 | 5/2002 | Jensen | |
| 6,537,239 B2 | 3/2003 | Mark | |
| 6,585,511 B2 | 7/2003 | Dragan et al. | |
| D496,999 S | 10/2004 | Dragan et al. | |
| D504,948 S | 5/2005 | Dragan et al. | |
| 6,957,958 B2 | 10/2005 | Rowe et al. | |
| 6,988,892 B2 | 1/2006 | Dragan et al. | |
| 7,040,893 B2 | 5/2006 | Fischer | |
| D527,457 S | 8/2006 | Dragan et al. | |
| 7,179,085 B2 | 2/2007 | Dorsey et al. | |
| 7,198,623 B2 | 4/2007 | Fischer et al. | |

* cited by examiner

*Primary Examiner*—David J Walczak
(74) *Attorney, Agent, or Firm*—Geoffrey E. Dobbin

(57) ABSTRACT

A delivery tip for flowable materials with bristles extending therefrom. The tip is a cannula with a tapered outlet and features a bristle bundle with a binding disk that interfaces with the cannula at some point within the cannula but has a smaller cross-section than the cannula at that point. The bristle bundle then extends out of the tapered outlet. The delivery tip is connected to a material reservoir with flowable material. When positive pressure is applied to the reservoir, material then will flow through the cannula, around the disk, into the bristles and out the outlet for distribution to a desired surface.

13 Claims, 8 Drawing Sheets

DELIVERY TIP FOR FLOWABLE MATERIALS

CROSS-REFERENCES TO RELATED APPLICATIONS

This application is a Continuing-in-Part Application of prior filed U.S. Utility application Ser. No. 11/567,367, filed Dec. 6, 2006, now U.S. Pat. No. 7,476,049, and incorporates the same in its entirety by reference herein.

FIELD OF THE INVENTION

The present invention relates to the field of material dispensing means and more particularly relates to brush tip structure to aid in such dispensing.

BACKGROUND OF THE INVENTION

Brush tips for dispensing material, particularly in medical and dental fields, are known in the prior art. Usually such tips present a flocked spreading means or some form of bristling. The prior art demonstrates that such means are mounted on the external surface of the syringe, tools, or other apparatus used to dispense or distribute the material. Unfortunately, these prior methods have a number of difficulties. The first is the potentially meticulous process of mounting the flocked and fibrous spreading means. The second is the potential for a weaker hold of the device on such means while in use, i.e. shedding. The third is the potential for clogging the external fibrous spreading means, which usually accompanies more secure binding of the fibrous spreading means. Therefore, prior art devices have had to strike a balance between acceptable shedding and acceptable flow.

The present invention is a delivery tip mountable upon a material containment or dispensing means which contains bristles internally in a bundle. The bristles are bound by an elliptical disk that is inserted within and resides within a narrowing cannula. The elliptical disk eventually reaches a point in the cannula where its major axis matches a major axis of the cannula, but the disk's minor axis is smaller than the corresponding minor axis of the cannula. The bristles then extend out of the narrow tip of the cannula while the cannula's broader end is fashioned with attachment means for the desired containment structure The present invention represents a departure from the prior art in that the bristled delivery tip of the present invention allows for more secure bundling of the bristles while simultaneously allowing for effective fluidic distribution.

SUMMARY OF THE INVENTION

In view of the foregoing disadvantages inherent in the known types of delivery means, this invention provides an improved bristled delivery means for fluidic materials. As such, the present invention's general purpose is to provide a new and improved delivery tip that is readily attachable to known and later developed containment structures and provides secure hold of bristled spreading means while not hindering fluidic discharge of material.

To accomplish these objectives, the delivery tip comprises a cannula with a delivery tip, a bundle of bristles disposed within the cannula and extending from the delivery tip, and a binding, elliptical disk, not having the same cross-section as the cannula while binding the bundle of bristles. The relationship between the elliptical disk and the cannula is such that at some point along the cannula, the major axis of the disk and the major axis of the cannula are the same, thereby preventing the disk from further progression down the cannula. However the minor axis of the disk is still smaller than the corresponding minor axis of the cannula, providing space for the material to flow around the disk. The cannula may, of course, be round, but in either event, the cross-section of the disk must be smaller than the cross-section of the cannula at the point of contact. Attachment means to a source or reservoir of flowable or fluidic material should also be provided, but those exact means will be dependent upon the means used on the reservoir (e.g. mating threaded means, luer lock, snap-fit, etc.).

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

With reference now to the drawings, the preferred embodiment of the delivery tip is herein described. It should be noted that the articles "a", "an", and "the", as used in this specification, include plural referents unless the content clearly dictates otherwise.

Figure 1:
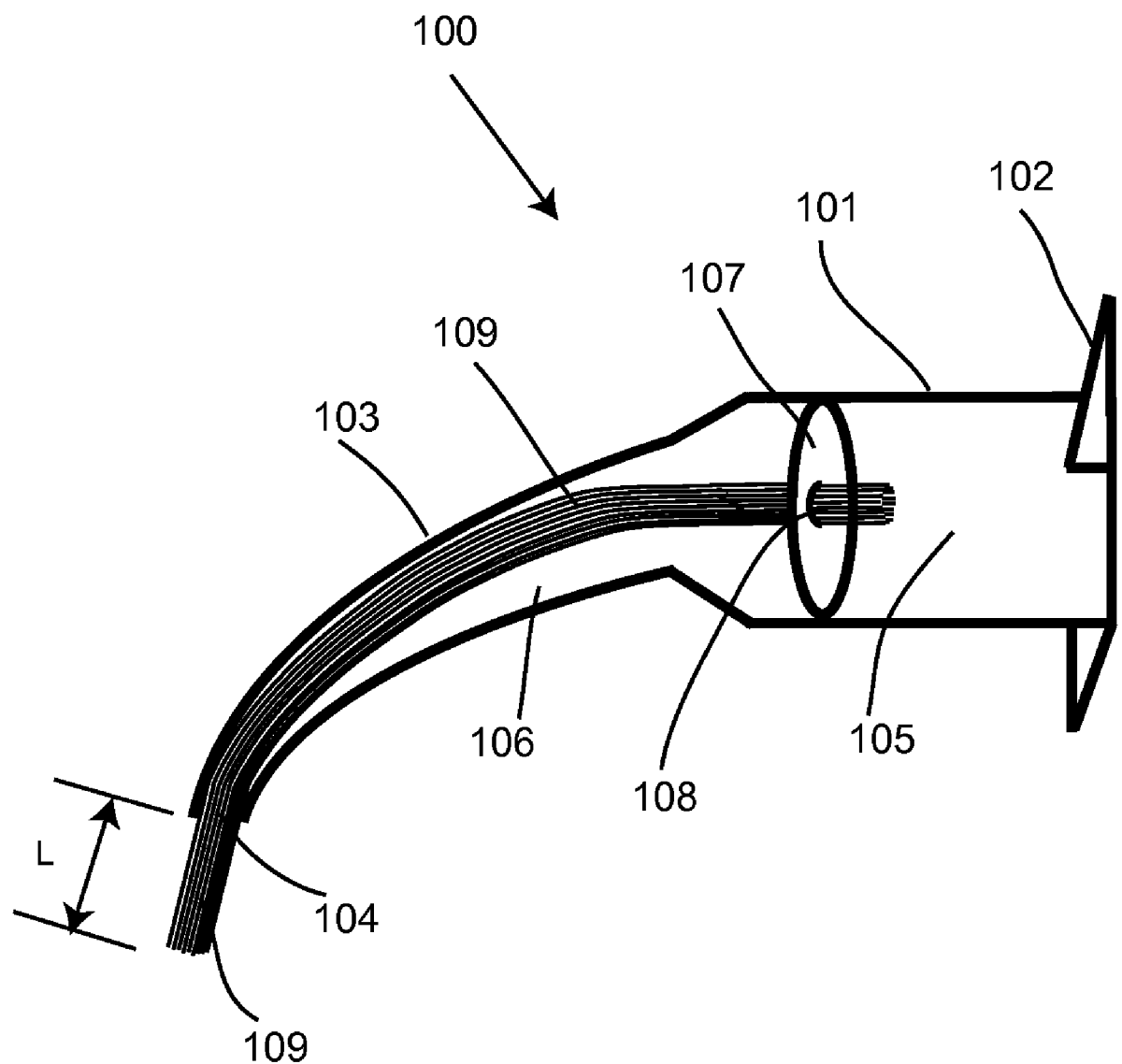
FIG. 1 is a transparent side plan view of one embodiment of the present invention, using a luer lock connection means.

With reference to FIG. 1, 100 is a brush tip according to the present invention in luer lock format. A relatively large cannula 101 is fashioned with a luer lock thread 102. The cannula 101 is graded 103 to a smaller outlet 104. The larger portion of the cannula 101 defines an interior 105 while the graded portion 103 defines an interior 106 with a decreasing cross-section. Fiber bundle 109 is threaded through the interior 106 of the graded cannula portion 103 and out the outlet 104. Bundle 109 is bound with a thin elliptical disk 107 with a hole 108, through which the bundle 109 is inserted. The disk 107 is mechanically pushed into the cannula 101 and is not able to be moved through the graded cannula portion 103. The diameter of fiber bundle 109 is smaller than diameter of outlet 104 and extrudes out of the outlet 104 for a given length L. As a preference, the extrusion length of fiber bundle from the outlet 104 should be larger than 0.5 mm, though any length is possible depending on desired specifications.

Figure 2:
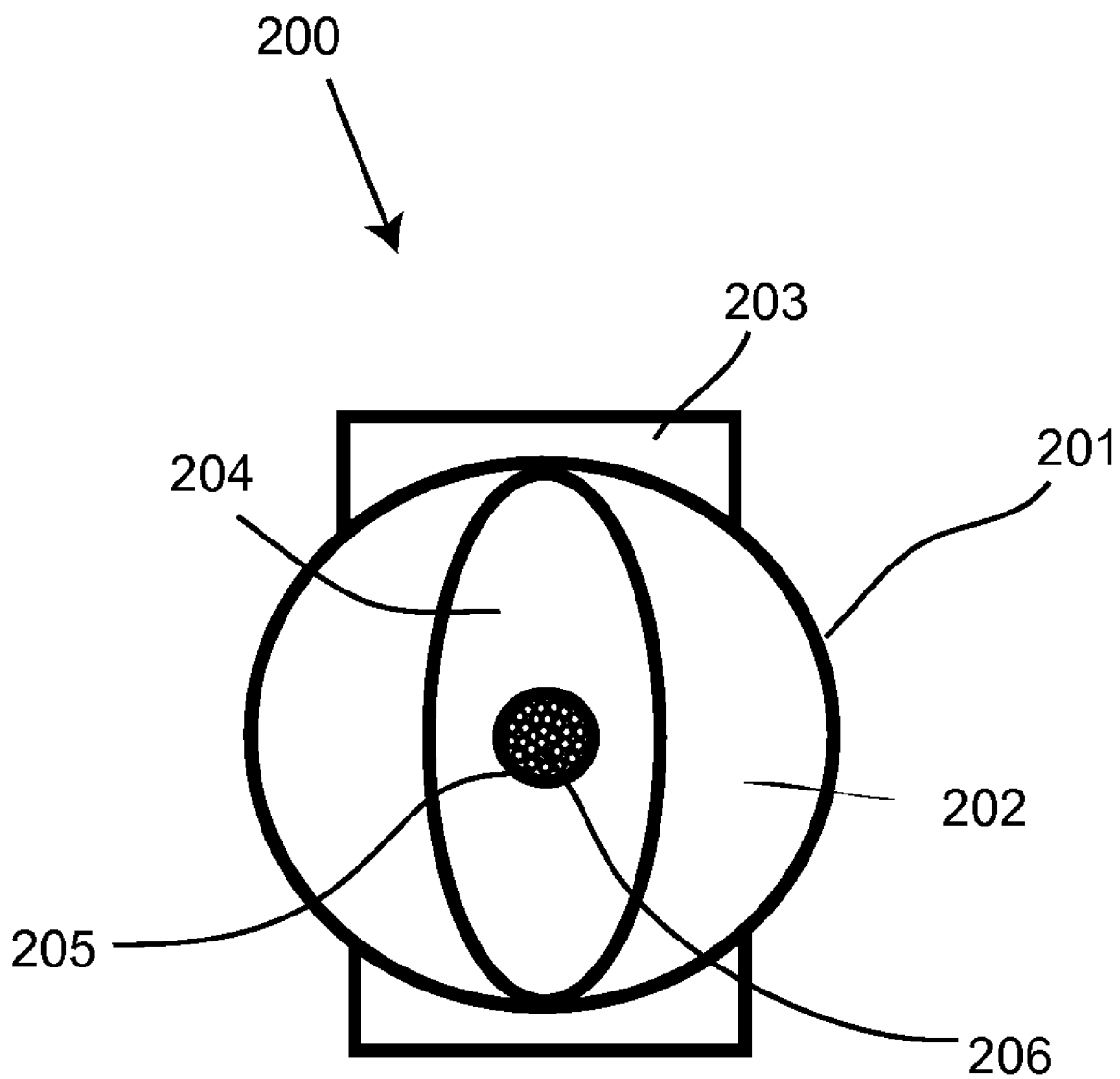
FIG. 2 is a real plan view of the embodiment depicted in FIG. 1.
Figure 4:
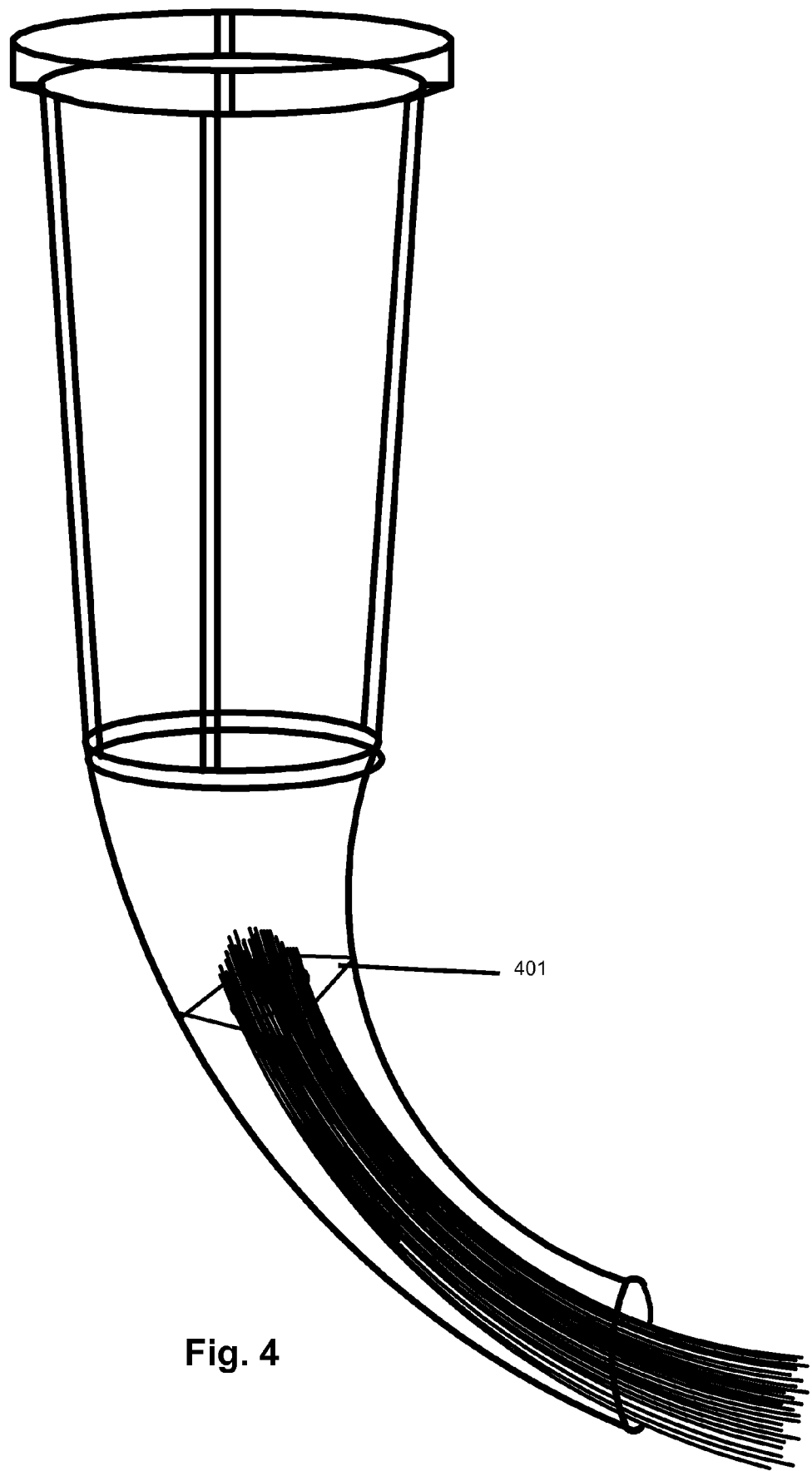
FIG. 4 is a transparent perspective view of the invention utilizing a square binding disk.

Referring to FIG. 2, 200 is end view of invented tip where 201 is wall of large cannula defining open space 202 inside the large cannula. Luer lock thread 203 is positioned on the outer end of the cannula. Elliptical disk 204 is mechanically set against the wall of cannula with fiber bundle 206 inserted into hole 205. The major axis of the disk 204 at that point matches, or is slightly larger than, the major axis of the cannula, while the minor axis is smaller than the corresponding axis of the cannula. The cannula may be round, as depicted in the figures, but may be of any shape, including non-elliptical ones, so long as the relation between the cannula and the disk 204 holds true, i.e. the disk has a smaller cross-section than the cannula, but simultaneously has a means to interface with the walls of the cannula. The diameter of fiber bundle is slightly larger than diameter of hole 205, thus fiber bundle is securely fixed with disk 204. The disk 204 is mechanically pushed into cannula (the fibers being threaded through the outlet 104) and since it has a major axis that is larger than the diameter of the outlet 104, will not move entirely through the cannula. Disk 204, being elliptical while the cannula is circular, allows material to flow around disk 204 with little or no hinderance. It should be noted that the luer lock depicted is only an example as other connection means may be used, such as a threaded interface, a snap-fitting interface, or any other interface known or later conceived in the art, without departing from the scope of the invention. It should also be noted that the disk may be of any shape that would lend itself to interfacing with the cannula while having a smaller cross-sectional area, such as the square disk 401 illustrated in FIG. 4. All that is required is that the disk must make contact with the wall of the cannula at a given point so as to be mechanically secured in place while simultaneously having a smaller cross-sectional area than the cannula at that point. As such, the term "disk" should not be seen as limiting to a round or elliptical shape. FIGS. 8a through 8h illustrate four different possible shapes (a triangle, a square, a five-pointed star, and an eight-pointed star, a hexagon, a pentagon, a rounded rectangle and a clover-like shape respectively), though any shape that meets the above referenced requirements, be they ellipses, polygons (like FIGS. 8a, 8b, 8e, or 8f), star shapes (like FIGS. 8c and 8d) or other free-form shapes (like shown in FIGS. 8g and 8h) would suffice.

Figure 3:
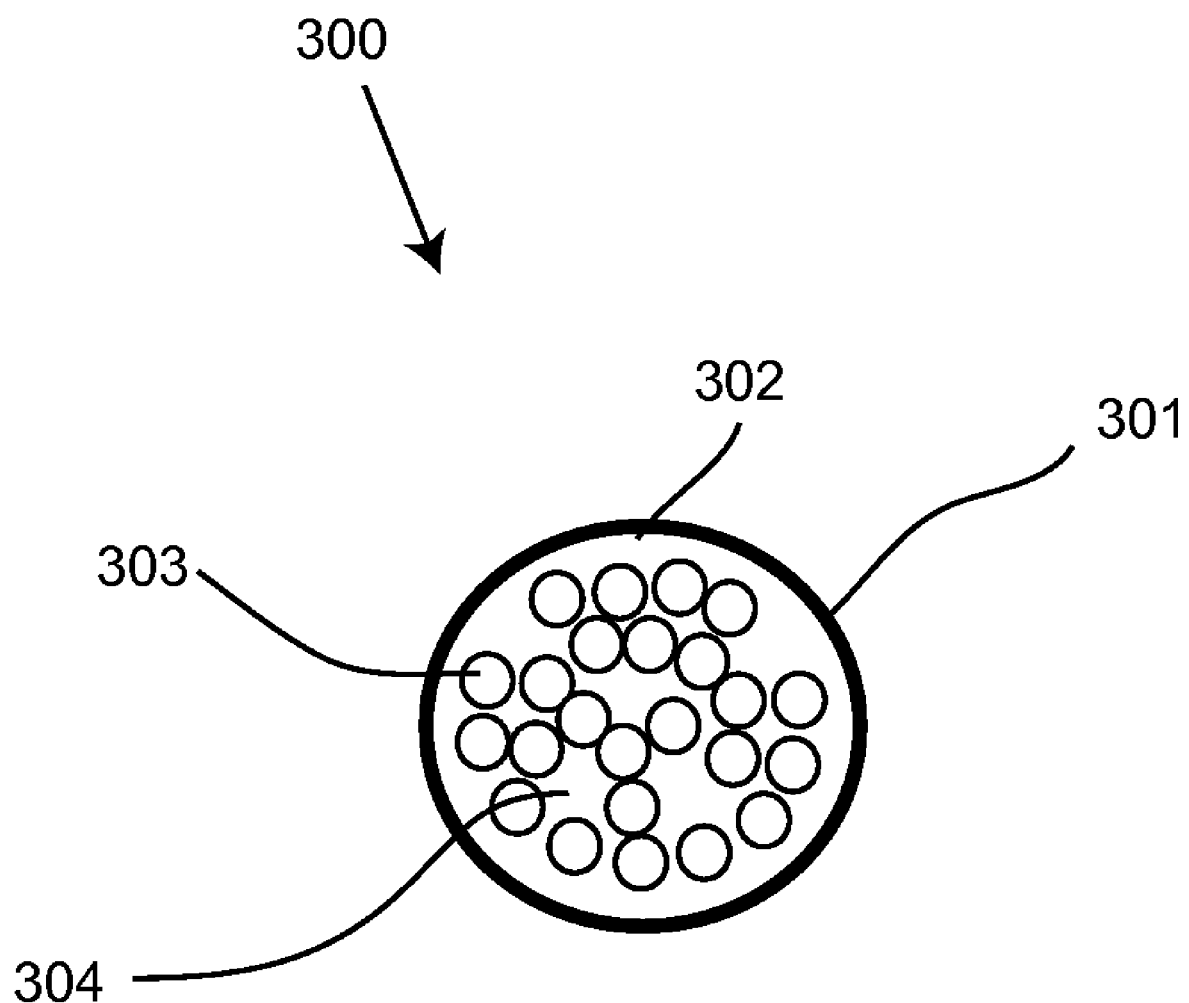
FIG. 3 is an end view of the bristled tip of the embodiment depicted in FIG. 1.

FIG. 3 depicts a front plan view of the tip 300, where 301 is the wall of smaller portion of the cannula and 303 is the fiber bundle. Open space 304 is left within the fiber bundle 303 as the diameter of fiber bundle 303 is smaller than inside diameter of the wall 301. The material will pass through the fiber bundle 303 through space 304. The total number of fibers will determine the diameter of fiber bundle 303 and also determine the size of space 304. Therefore, by controlling total numbers of fibers in the bundle, the flow of the material can be controlled.

Figure 5:
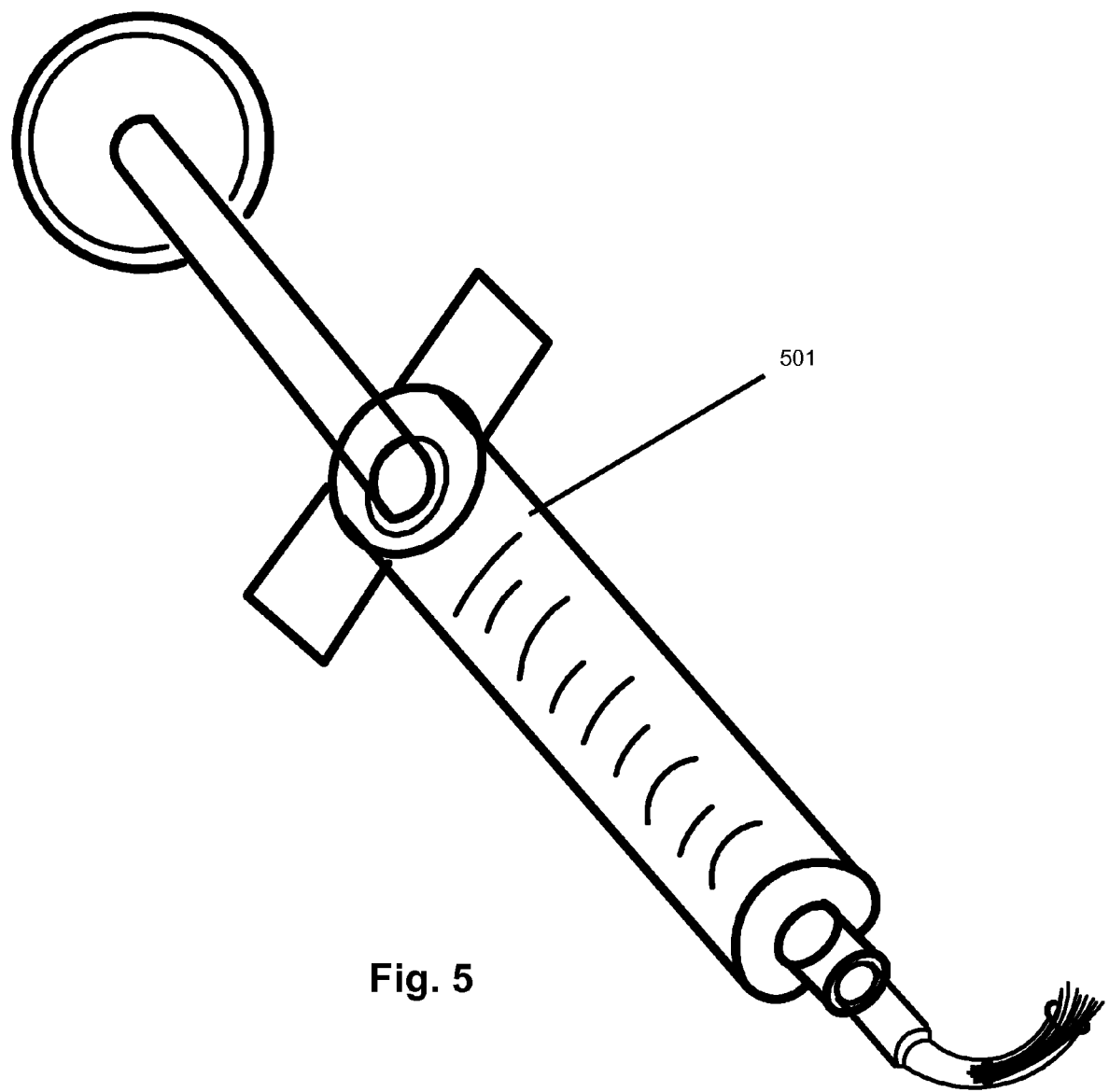
FIG. 5 is a perspective view of the invention installed on a syringe.
Figure 6:
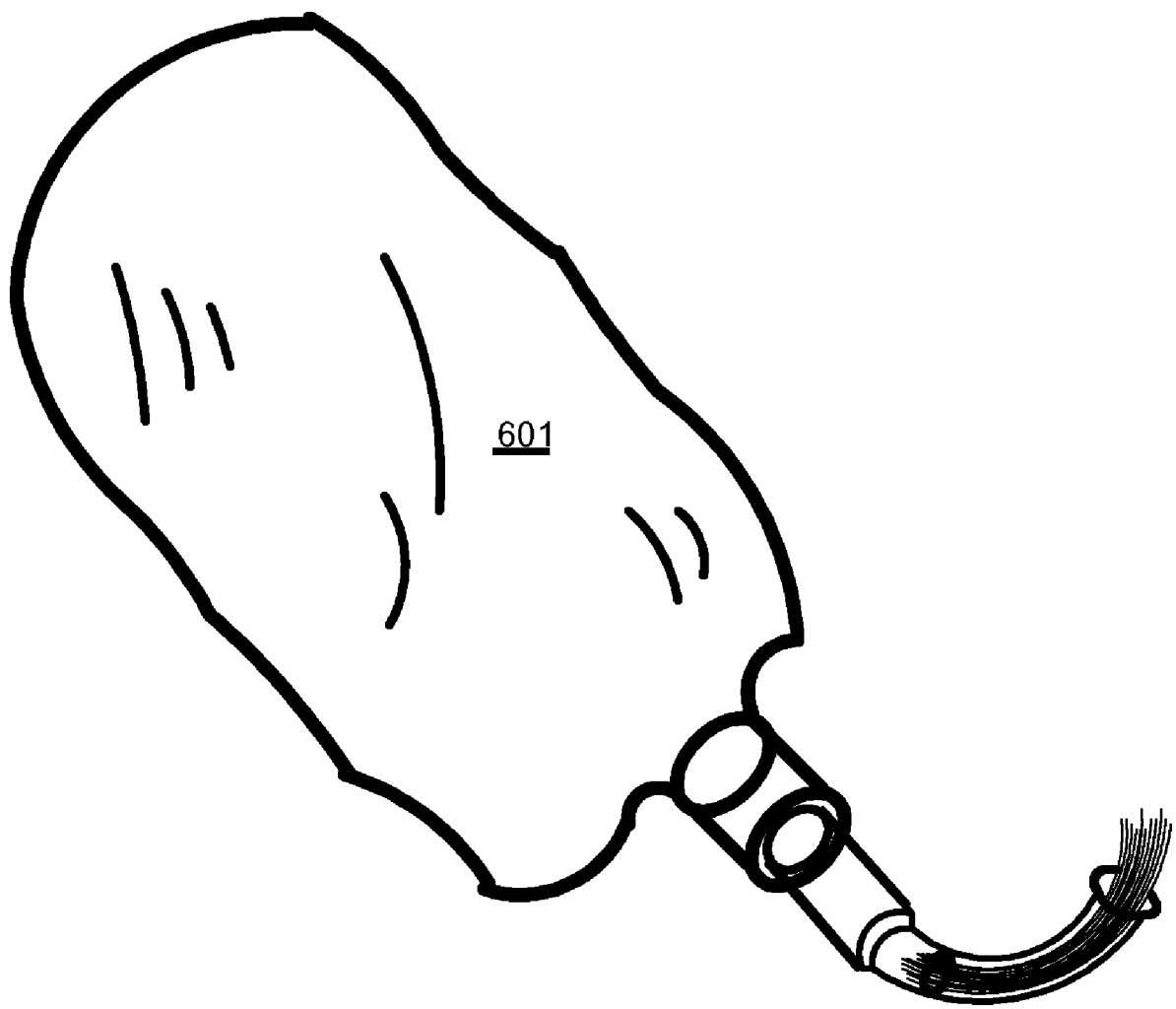
FIG. 6 is a perspective view of the invention installed on a reservoir bag.
Figure 7:
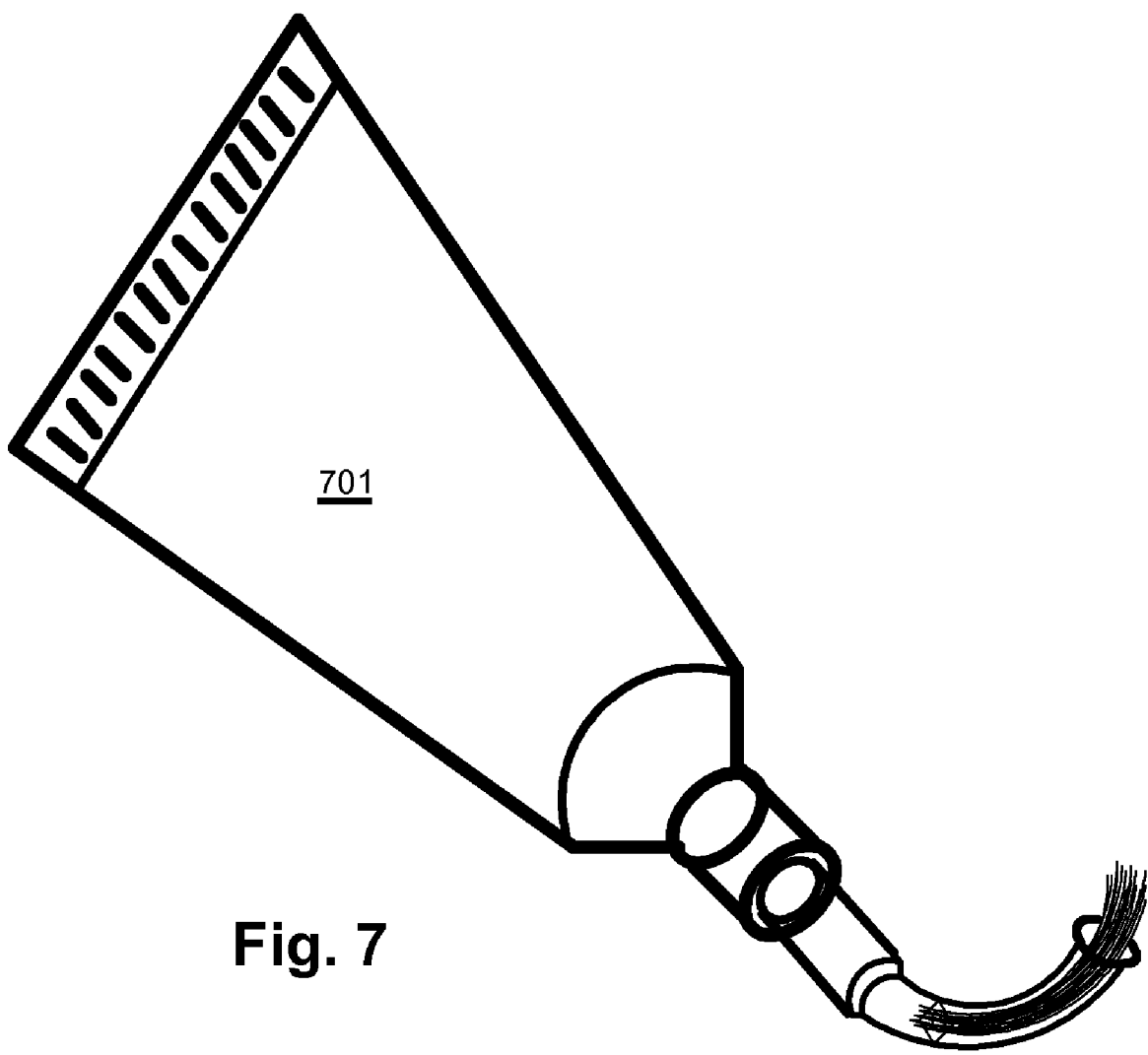
FIG. 7 is a perspective view of the invention installed on a bottle.
Figure 8A:
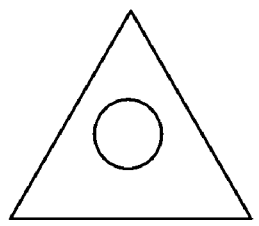
FIGS. 8a-8h are top plan views of example disks of varying shapes.
Figure 8B:
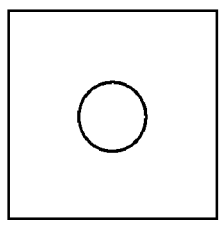
Figure 8C:
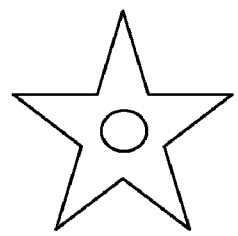
Figure 8D:
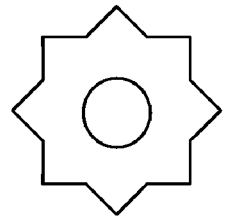
Figure 8E:
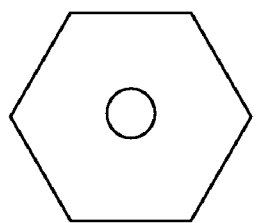
Figure 8F:
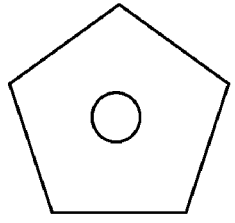
Figure 8G:
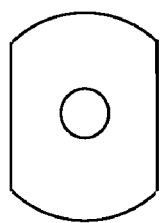
Figure 8H:
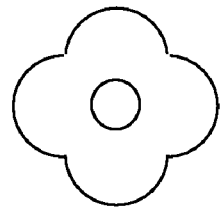

When the described tip is attached to a syringe or other container containing flowable material, as depicted in FIGS. 5-7 being a syringe 501, reservoir bag 601, and bottle 701, positive pressure will make the material flow into the inside space of the cannula and then into the smaller open space, then around the disk and then through the fiber bundle and out the cannula tip. Since the diameter of fiber bundle is less than diameter of smaller cannula outlet, the flowable material will flow through the fiber bundle, but yet the fiber bundle will maintain its position within the tip and its structural integrity. The extrusion fiber bundle brush is then used to spread or otherwise distribute the flowable material to the application surface. Material flow will be affected by both the relative cross-sectional sizes of the disk and the interior of the cannula and the open space left between the fiber bundle and the tip opening. These ratios may be varied for different intentions and purposes and as such a best mode is dependent upon these purposes. It is sufficient to describe the invention to say that a more viscous fluid may require more space while a less viscous one less space.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A delivery tip for flowable materials, the tip comprising:
 a. a cannula having an outlet; and
 b. a bristle bundle of a diameter smaller than the outlet, bound near one end with a flat disk; and
 c. the disk being wedged into the cannula at a point where it has a cross-sectional area less than a cross-sectional area of an interior of the cannula at that given point;
 wherein, the bristle bundle is threaded through the cannula such that bristles from an end opposite the disk extend out of the outlet.

2. The delivery tip of claim 1, further comprising attachment means opposite the outlet.

3. The delivery tip of claim 2, the attachment means being selected from the list of attachment means consisting of: threaded interfaces, snap-fit interfaces, and a luer lock interface.

4. The delivery tip of claim 1, the bristles extending out of the outlet by at least 0.5 mm.

5. The delivery tip of claim 4, further comprising attachment means opposite the outlet.

6. The delivery tip of claim 5, the attachment means being selected from the list of attachment means consisting of: threaded interfaces, snap-fit interfaces, and a luer lock interface.

7. The delivery tip of claim 1, the disk shape being selected from the list of disk shapes consisting of: ellipses, polygons, free-form shapes, and multi-pointed stars.

8. The delivery tip of claim 7, further comprising attachment means opposite the outlet.

9. The delivery tip of claim 8, the attachment means being selected from the list of attachment means consisting of: threaded interfaces, snap-fit interfaces, and a luer lock interface.

10. The delivery tip of claim 7, the bristles extending out of the outlet by at least 0.5 mm.

11. The delivery tip of claim 10, further comprising attachment means opposite the outlet.

12. The delivery tip of claim 11, the attachment means being selected from the list of attachment means consisting of: threaded interfaces, snap-fit interfaces, and a luer lock interface.

13. The delivery tip of claim 1, the cannula being graded and decreasing in internal cross-sectional area as a function of decreasing distance from the outlet.

* * * * *